United States Patent [19]

Harada et al.

[11] Patent Number: 4,731,050
[45] Date of Patent: Mar. 15, 1988

[54] ACUPRESSURE TYPE MOXIBUSTION CASE

[76] Inventors: Minoru Harada, 963, Myohoji Aza Kitsune, Suma-Ku, Kobe; Hiroji Harada, 1576-18 Nozoe, Harima-cho, Kakogun, Hyogo, both of Japan

[21] Appl. No.: 883,890

[22] Filed: Jul. 9, 1986

[51] Int. Cl.⁴ ............................................. A61M 37/00
[52] U.S. Cl. ..................................... 604/24; 604/291; 128/399
[58] Field of Search .......................... 604/23, 291, 24; 128/399, 400

[56] References Cited

U.S. PATENT DOCUMENTS 1,831,669 11/1931 Kōno .................................... 604/291
4,325,371 4/1982 Atsumi ................................ 604/291
4,604,088 8/1986 Nottbohm ........................... 604/291

Primary Examiner—John D. Yasko
Assistant Examiner—J. L. Kruter
Attorney, Agent, or Firm—Jordan and Hamburg

[57] ABSTRACT

An improved moxibustion case also performs acupressure. The moxibustion case is constructed with a cylindrical body having a moxa holder attached to its end portion to hold a cylindrical moxa slidably in its longitudinal direction and a cap member having a rear end portion fitted rotatably to the front end portion of the cylindrical body and a front wall having a discharge opening for a moxa combustion gas to treat a desired part of the body. Air supply openings at the circumference and along the length of the cylindrical body near its middle to control the moxa fire-force.

20 Claims, 14 Drawing Figures 4,731,050

ACUPRESSURE TYPE MOXIBUSTION CASE

BACKGROUND OF THE INVENTION

The present invention relates to an improved moxibustion case which may also have the function of an acupressure, and more particularly to a novel acupressure-type moxibustion case which can be simultaneously used for superior moxibustion therapy and superior acupressure therapy by touching moxa combustion gas directly to an affected part to heat it and penetrate the effective ingredient contained in moxa and raw loquat leaves into the hypodermic portion of the affected part.

The raw loquat leaf has been nicknamed said "Needless for Doctor" and utilized for health improvement in various parts of Japan. For instance, several effective folk remedies utilizing loquat leaves have been transmitted and utilized from generation to generation. Specifically, one folk remedy is the touching method, in which the surfaces of two sheets of loquat leaves are repeatedly and quickly put on an affected part just after broiling them over a slow fire and then rubbing them against each other. Other methods include the drinking method and the hot-water bath cure method. Further, relatively recently, it has been ascertained that the loquat leaf contains the substance "amygdalin", from which vitamin B17 (Laetrile) can be extracted and which has the superior effect of purifying the blood by vapor penetration into the body through the skin.

On the basis of this knowledge, the present inventors have already invented a moxibustion case which improved the moxibustion effect by utilizing the vaporized effective ingredient of raw loquat leaves in addition to the moxa combustion gas, and filed Japanese Utility Model Application No. 52-80716 (Sho52(1977), Laid-Open Publication No. 54-7591 (Sho54 (1979). However, this moxibustion case for loquat leaf therapy has suffered from one or more defects in its operation and usage, which prevent its wide acceptance. That is, in the previous moxibustion case, it was necessary to almost always operate an inside pump including a slidable rear end cap in order to control the fire force of moxa and increase the pressure of moxa combustion gas to a desired level during usage. Also, the previous case assumed that raw loquat leaves were always readily available. Therefore, both hands were needed to operate the pump, and the case was useless if raw loquat leaves could not be obtained.

SUMMARY OF THE INVENTION

The present invention has for an object to eliminate disadvantages, inconveniences and defects in the previous moxibustion case and provides an improved acupressure type moxibustion case which is simple in construction; which can be used conveniently and safely by old men, women and children; which can be adjusted to treat the same affected part for a long time at a comfortable and uniform temperature and pressure, differing from spot moxibustion that totally heats the affected part strongly and in a short time, gives pain to the patient and leaves scars on the skin; which can be used without hindrance even if raw loquat leaves cannot be obtained because the extract from them is prepared for the therapy; which increases the curative value by penetrating the effective ingredient of a moxa and a loquat leaf sufficiently into the affected part; and which provides a superior moxibustion effect by utilizing moxa combustion gas disregarded in prior art moxibustion case and moxacantery utensil and provides easy temperature adjustment of the moxicombustion.

BRIEF DESCRIPTION OF THE DRAWINGS

The foregoing and other objects and attendant advantages of the present invention will be readily appreciated as the same become better understood by reference to the following detailed description of a specific embodiment when considered with the accompanying drawings, wherein.

DESCRIPTION OF THE PREFERRED EMBODIMENT

Figure 1:
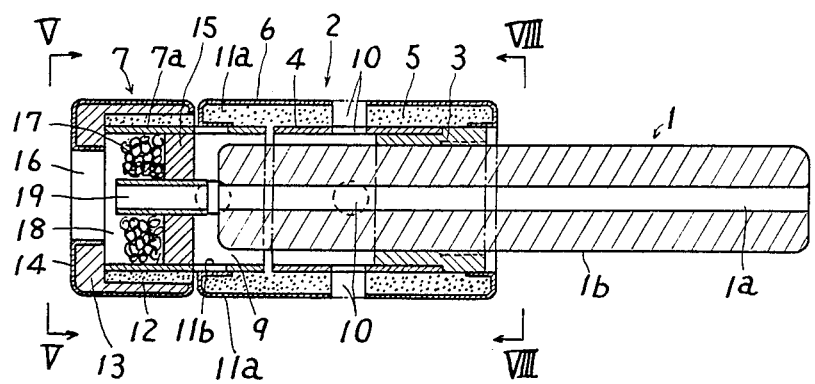
FIG. 1 is a longitudinal cross-sectional view of a moxibustion case in accordance with the present invention, provided with the first embodiment of a cap member.

In FIG. 1, FIG. 2, FIG. 3, FIG. 4, FIG. 5, FIG. 6, FIG. 7 and FIG. 8, numeral 1 indicates a cylindrical moxa which is formed to the following dimension, e.g. its length is 150 mm, its outside diameter is 25 mm and its bore is ab. 5 mm, by pressing very tightly, and which is wrapped by a damp-proofing strong thin paper. Numeral 2 indicates a cylindrical body which serves also for the handle of the moxibustion case and which comprises a moxa holder 3 made of light, anti-corrosive and comparatively inexpensive metal such as aluminium, an inside cylinder 4 incorporated in one therewith and a heat-insulator 5 such as asbestos cloth or glassfiber wound thereon to a suitable thickness and wrapped by a covering 6 such as soft velvet pasted onto it. As being understood in FIG. 1 and FIG. 2, an outside cylinder comprising the heat-insulator 5 wrapped by the velvet covering 6 of the cylindrical body 2 is extended in a suitable dimension in front of the inside cylinder 4. The cylindrical moxa 1 inserted into the central bore of the body 2 from its front end is retained slidably in front and in the rear in the longitudinal direction coaxially with the body 2, which is fixed firmly at a desired position (all the time) while the moxa is being used. Numerals 7 and 8 are exchangeable type cap members attached detachably and coaxially on the front end portion of the body 2. These two kinds of the cap members 7,8 have substantially the same dimension in outside diameter and inside diameter as the body 2 and a comparatively short length, and include inside cylinder 7a,8a made of the same material as inside cylinder 4, such as aluminium, extended backward from the rear end of the outside cylinder to a suitable dimension, for example, to a dimension substantially the same as or a little shorter than the length between the front end of inside cylinder 4 and the front end of the outside cylinder comprising the heat-insulator 5 and the covering 6. Therefore, either of cap members 7,8 is to be engaged rotatably, firmly and selectively by inserting the protruding portion of the inside cylinder 7a,8a into the front bore of the body 2. In accordance with the intended use of this moxicombustion case, at the circumference of the middle position along the length of the cylindrical body 2 and at its suitable engaging position with the cap member 7,8, air supply openings 10,11 having a suitable size and configuration (four numbers of small circular openings in both depicted embodiments) are bored to communicate with a space 9 formed between the cylindrical moxa 1 inserted and retained through the body 2 and the inside cylinders 4,7a,8a. Each air supply opening 11 is controlled continuously from full opening to entirely closed by turning either the cylindrical body 2 or the cap member 7,8 to the other. That is, four openings 11a having the same configuration and size at the front end portion of the body 2 can be aligned completely in the radial direction with four openings 11b in the protrusion portion of the inside cylinder 7a,8a by turning them into alignment with each other suitably.

In the front flat wall of the cap member 7,8, which is touched directly or indirectly, that is, which puts raw loquat leaf on it to affected parts of patients, one or more openings are bored to a suitable size in order to discharge the combustion gas of the cylindrical moxa, the front end of which is fired. Further detailing this construction, the cap member 7 comprises the inside cylinder 7a made of aluminum, a heat insulator 12 such as asbestos cloth wound to a suitable thickness on the fore side thereof, a thermostable rubber layer having suitable elasticity to improve the sense of touch and being coated with acrylic ester and a partition wall 15 made of aluminum and fixed at the front of the openings 11b within the inside cylinder 7a in order to use the extract from loquat leaves instead of raw loquat leaves. That is, between the partition wall 15 and the front wall having a comparatively large central opening 16, chamber 18 is formed for vaporizing the extract from the loquat leaves absorbed and retained in suitable quantities by a retaining material 17 such as absorbent cotton, a sponge and urethane-foam. In order to communicate the chamber 18 with the space 9 within the body 2, there is provided a small-caliber pipe 19 made of aluminum, the same material as the wall 15, which passes through the wall 15 perpendicularly and coaxially with the cap member 7. Further, the front end of the pipe 19 is opened at a position spaced a suitable distance backward from the front wall of the cap member 7 within the chamber 18. (referring to FIG. 1, FIG. 3 and FIG. 5)

Figure 2:
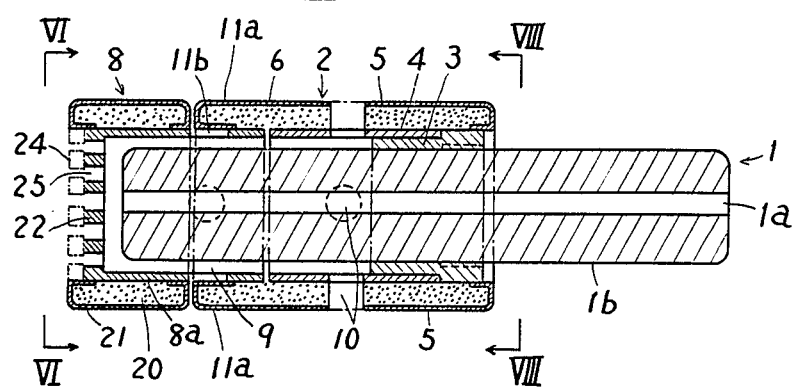
FIG. 2 is a longitudinal cross-sectional view of a moxibustion case in accordance with the present invention, provided with the second embodiment of a cap member.
Figure 3:
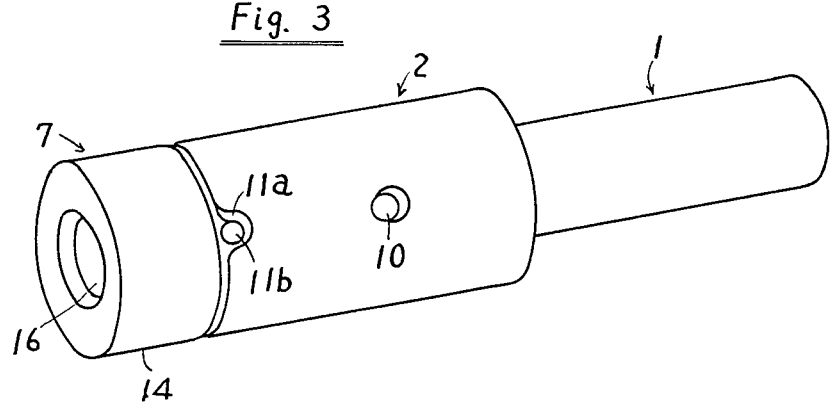
FIG. 3 is a perspective plan view of the moxibustion case of FIG. 1.
Figure 1A:
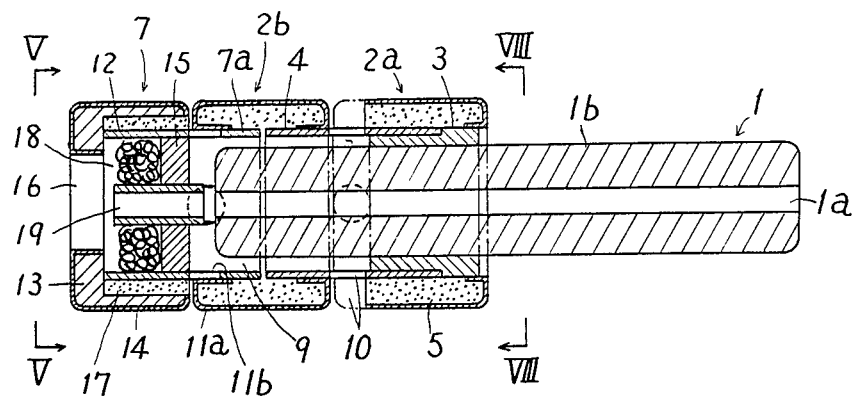
FIG. 1A is a longitudinal cross-sectional view of another embodiment of a moxibustion case similar to FIG. 1.
Figure 2A:
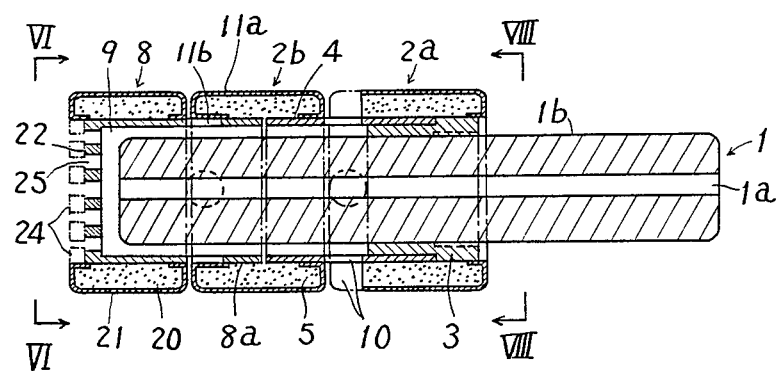
FIG. 2A is a longitudinal cross-sectional view of another embodiment of a moxibustion case similar to FIG. 2.
Figure 3A:
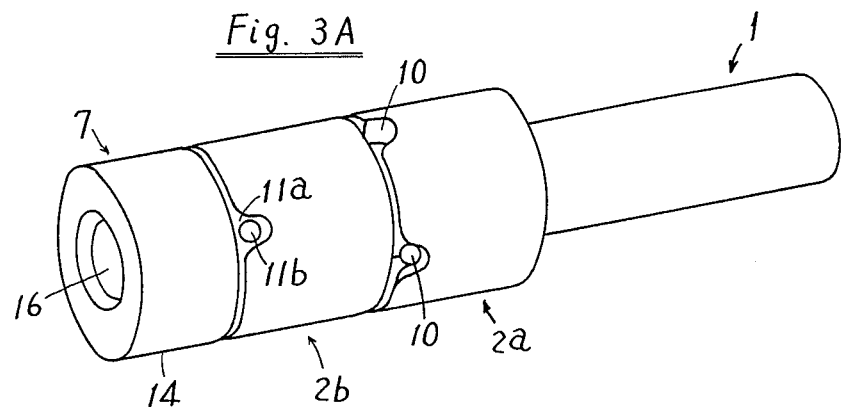
FIG. 3A is a perspective plan view of the moxibustion case of FIG. 1A.
Figure 4A:
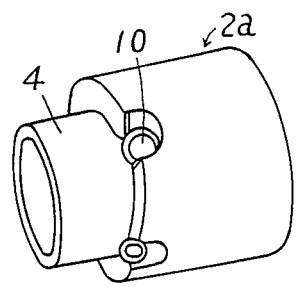
FIG. 4A is a perspective view of an end segment of a cylindrical case body.
Figure 4B:
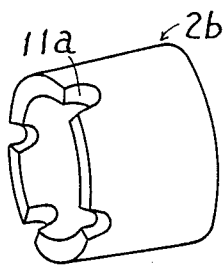
FIG. 4B is a perspective view of a middle segment of a cylindrical case body.
Figure 5:
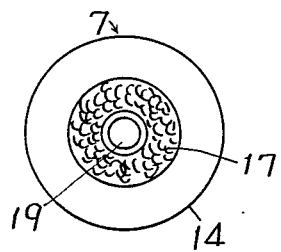
FIG. 5 is a frontal end view taken from the line V—V in FIG. 1 and FIG. 1A.
Figure 6:
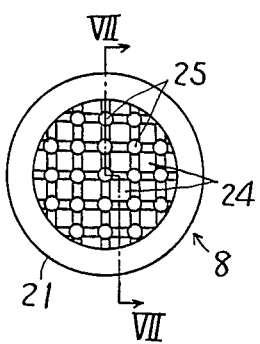
FIG. 6 is a frontal end view taken from the line VI—VI in FIG. 2 and FIG. 2A.
Figure 7:
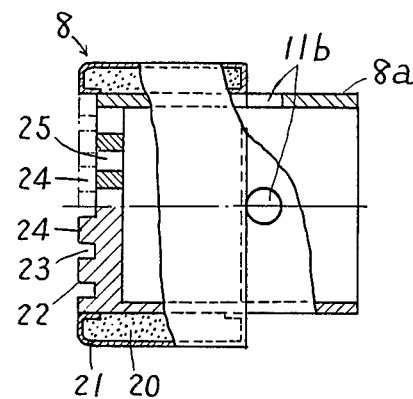
FIG. 7 is a longitudinal partial cross-sectional view on a larger scale taken along the line VII—VII in FIG. 6.
Figure 8:
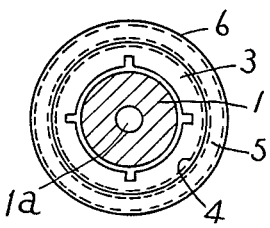
FIG. 8 is a cross-sectional view taken along the line VIII—VIII in FIG. 1A and FIG. 2A

On the other hand, another type of cap member 8 is constructed to be used together with raw loquat leaves, that is, comprising inside cylinder 8a made of aluminium, which has substantially the same sectional configuration and the same dimension as the inside cylinder 4 of the cylindrical body above described, and a heat insulator 20 such as asbestos cloth wound in a suitable thickness as an outside cylinder on the front portion thereof and wrapped by a covering 21 such as velvet according to the same principle as the cylindrical body 2. In front wall 22 made of a suitable thickness of aluminium and integrated with the front end of inside cylinder 8a there are provided plural parallel grooves 23 cut vertically and horizontally at regular intervals at a depth of about half the thickness of the wall 22 from its front surface, for instance, laid out at right angles like the squares of a checkerboard. There are also provided small openings 25 bored at cross points of grooves 23 and surrounded by small protrusions 24 formed at regular intervals by the groove cutting. The front end surfaces of the small protrusions 24 are arranged on the same level as the ring-shaped front surface of the outside cylinder formed by the heat insulator 20 and the velvet covering 21, as indicated in FIG. 2, FIG. 6 and FIG. 7. In another embodiment besides the integrated cylindrical body 2, the body may be constructed of two parts 2a, 2b fitted removably with each other as occasion demands, as shown in FIG. 1A, FIG. 2A, FIG. 3A and FIG. 4A.

To operate the above described embodiment of the acupressure type moxibustion case, the cylindrical moxa 1 is inserted to a suitable depth from the back end of the cylindrical body 2, fired at its front end and fixed at a suitable position along its longitudinal direction by moxa holder 3 after increasing the fire force by breathing upon it and confirming the stabilization of the fire force. In case of loose fitting to the body 2, it could be fixed by putting toothpicks, etc. between them.

After fitting the cap member 7,8, if necessary, the fire force of moxa 1 is increased by breathing upon it through the central opening 16 and the pipe 19, or through the plural openings 25, or by breathing upon it through the openings 11a,11b registered with each other by turning either the cylindrical body 2 or the cap member 7,8 to the other and thus communicated with each other.

If loquat leaves cannot be obtained, the extract from loquat leaves might be used. After pouring suitable quantities of the extract into the retaining material 17 such as absorbent cotton filled within the vaporizing chamber 18 of the cap member 7 by using a squirt, the front surface of the cap member 7 is placed on the affected part directly with suitable pressure by holding the body with thumb and index finger. When using loquat leaves, after removing stains from the leaves with a wetted cloth, if necessary, one or two sheets of leaves are put between the front surface of the cap member 8 and the affected part according to the fire force. That is, the front surface is placed on the affected part indirectly.

In the former case, combustion gas of the cylindrical moxa 1 enters into the chamber 18 to heat and vaporize the extract contained in the extract retaining material 17 and generates a high temperature gas containing the effective ingredients of the moxa and the loquat leaves. This high temperature gas regulated at a suitable temperature for the moxicombustion therapy is applied to the affected part efficiently during a desired time by the moxicombustion case. In the latter case using the cap member 8, combustion gas of the cylindrical moxa 1 regulated at a comparatively high temperature enters the grooves 23 through the openings 25, penetrates the raw loquat leaves pressed against the affected part by the protrusions 24 and the front surface of the outside cylinder, vaporizes the effective ingredients contained in the raw loquat leaves by its heat and brings them to the affected part in combination as one.

Therefore, in either case, in addition to the acupressure-type moxibustion effectiveness, the curative value is increased by penetrating the effective ingredient of a moxa and a loquat leaf sufficiently into the affected part.

The fire force control of the cylindrical moxa 1 can be done by increasing or decreasing the degree of opening of the air supply openings 11 bored at both fitting portions of the cap member 7,8 and the cylindrical body 2,2b. When the cylindrical moxa 1 becomes too short to be held at a suitable position by the moxa holder 3 as a result of long time usage, it could be connected at its rear end with another new cylindrical moxa by a binding agent and used without any loss.

Figures 9, 10:
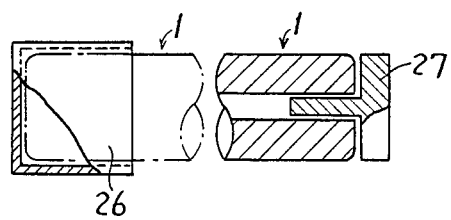
FIG. 9 is a partially broken cross-sectional view of an extinguishing cap.
FIG. 10 is a longitudinal cross-sectional view of a cylindrical moxa and an extinguishing and fire-force controlling plug.

When moxibustion therapy is interrupted or finished, once the cap member 7,8 is removed, and after an extinguishing cap 26 made of aluminium is put on the fired front end of the cylindrical moxa 1 and an extinguishing plug is inserted in the rear end opening of its longitudinal through hole 1a, as indicated in FIG. 9 and FIG. 10, the cap member 7,8 is restored to its normal condition. Otherwise, after removing the cylindrical moxa 1 from the cylindrical body 2,2a,2b, the moxa 1 is put into a china pot or a can (not shown in the figures), while the extinguishing cap and extinguishing plug are put on for the sake of safety. By the way, besides extinguishing the fire of the moxa 1 by shutting out air for its combustion, the plug 27 can be used for controlling the fire force during therapy.

It is understood that the above-described embodiment of the acupressure-type moxibustion case is only illustrative, and that various modifications and steps may be made by those skilled in the art without departing from the spirit and scope of the invention as claimed.

What is claimed is:

1. An acupressure-type moxibustion case comprising:
a cylindrical body having a rear end portion and a front end portion; a moxa holder attached to the rear end portion of the cylindrical body; a cylindrical moxa slidably held by said moxa holder in a longitudinal direction coaxially within said cylindrical body, said cylindrical moxa being removably inserted into said moxa holder from the rear end portion of the cylindrical body and forming a space between said cylindrical moxa and said cylindrical body in the front end portion of said cylindrical body;
a cap member having a rear end portion removably, rotatably and coaxially fitted to the front end portion of said cylindrical body to engage said cylindrical body, said cap member having a front wall for contact with affected body parts and an opening in said front wall communicating with said space formed between said cylindrical body and said cylindrical moxa for discharging combustion gas from firing said cylindrical moxa, wherein said front wall of said cap member is made of aluminium and comprises a plurality of small protrusions formed and arranged at regular intervals in said front wall and flush with said front wall, and wherein said discharge opening for said moxa combustion gas comprises a plurality of small openings recessed between said protrusions; and
first air supply openings formed along the length of said cylindrical body between said rear end portion and said front end portion and second air supply openings formed along the length of and in said cap member where sid cap member engages the front end portion of said cylindrical body, wherein said first and second air supply openings communicate with the space formed between said cylindrical moxa and said cylindrical body.

2. An acupressure-type moxibustion case according to claim 1, wherein the amount of air supplied to said space through said second air supply openings is varied from maximum to zero by rotating said cap member and said cylindrical body relative to each other.

3. An acupressure-type moxibustion case according to claim 1, wherein said cap member further comprises an inside cylinder, a heat insulator wound around said inside cylinder, a thermostable rubber layer having suitable elasticity covering said heat insulator, and a chamber within said inside cylinder containing a retaining material for absorbing and retaining loquat leaf extract, said chamber vaporizing the loquat leaf extract absorbed and retained by the retaining material, said chamber being defined by said inside cylinder, the front wall and discharge opening of said cap member, and a partition wall opposite said discharge opening, and further including a small-caliber metal pipe within said cap member for communicating said chamber with the space formed between said cylindrical moxa and said cylindrical body, said metal pipe having a rear end secured to and passing perpendicularly through said partition wall and a front end terminating within said chamber at a position spaced a suitable distance back from the front wall and discharge opening of said cap member.

4. An acupressure-type moxibustion case according to claim 3, wherein said inside cylinder of said cap member comprises aluminium and said heat insulator comprises asbestos cloth.

5. An acupressure-type moxibustion case according to claim 1, wherein the moxa holder of said cylindrical body comprises a metal and wherein said cylindrical body comprises an inside cylinder formed integrally around said moxa holder and a heat-insulator wound around said inside cylinder to a suitable thickness.

6. An acupressure-type moxibustion case according to claim 5, wherein said moxa holder metal is aluminium and said heat insulator comprises asbestos cloth.

7. An acupressure-type moxibustion case according to claim 1, wherein said cylindrical body comprises two sections detachably connected to each other.

8. An acupressure-type moxibustion case according to claim 1, wherein said cylindrical moxa is wrapped in a strong thin paper and includes a longitudinal central through-hole therein.

9. An acupressure-type moxibustion case comprising:
a cylindrical body having a rear end portion and a front end portion; a moxa holder attached to the rear end portion of the cylindrical body; a cylindrical moxa slidably held by said moxa holder in a longitudinal direction coaxially within said cylindrical body, said cylindrical moxa being removably inserted into said moxa holder from the rear end portion of the cylindrical body and forming a space between said cylindrical moxa and said cylindrical body in the front end portion of said cylindrical body;

a cap member having a rear end portion removably, rotatably and coaxially fitted to the front end portion of said cylindrical body to engage said cylindrical body, said cap member having a front wall for contact with affected body parts and an opening in said front wall communicating with said space formed between said cylindrical body and said cylindrical moxa for discharging combustion gas from firing said cylindrical moxa, wherein said cap member comprises an inside cylinder, a heat insulator wound around said inside cylinder, a thermostable rubber layer having suitable elasticity covering said heat insulator, and a chamber within said inside cylinder containing a retaining material for absorbing and retaining loquat leaf extract, said chamber vaporizing the loquat leaf extract absorbed and retained by the retaining material, said chamber being defined by said inside cylinder, the front wall and discharge opening of said cap member, and a partition wall opposite said discharge opening, and further including a small-caliber metal pipe within said cap member for communicating said chamber with the space formed between said cylindrical moxa and said cylindrical body, said metal pipe having a rear end secured to and passing perpendicularly through said partition wall and a front end terminating within said chamber at a position spaced a suitable distance back from the front wall and discharge opening of said cap member; and first air supply openings formed along the length of said cylindrical body between said rear end portion and said front end portion and second air supply openings formed along the length of and in said cap member where said cap member engages the front end portion of said cylindrical body, wherein said first and second air supply openings communicate with the space formed between said cylindrical moxa and said cylindrical body.

10. An acupressure-type moxibustion case according to claim 9, wherein the amount of air supplied to said space through said second air supply openings is varied from maximum to zero by rotating said cap member and said cylindrical body relative to each other.

11. An acupressure-type moxibustion case according to claim 9, wherein said inside cylinder of said cap member comprises aluminium and said heat insulator comprises asbestos cloth.

12. An acupressure-type moxibustion case according to claim 9, wherein the moxa holder of said cylindrical body comprises a metal and wherein said cylindrical body comprises an inside cylinder formed integrally around said moxa holder and a heat-insulator wound around said inside cylinder to a suitable thickness.

13. An acupressure-type moxibustion case according to claim 12, wherein said moxa holder metal is aluminium and said heat insulator comprises asbestos cloth.

14. An acupressure-type moxibustion case according to claim 9, wherein said cylindrical body comprises two sections detachably connected to each other.

15. An acupressure-type moxibustion case according to claim 9, wherein said cylindrical moxa is wrapped in a strong thin paper and includes a longitudinal central through-hole therein.

16. An acupressure-type moxibustion case comprising:

a cylindrical body having a rear end portion and a front end portion; a moxa holder attached to the rear end portion of the cylindrical body; a cylindrical moxa slidably held by said moxa holder in a longitudinal direction coaxially within said cylindrical body, said cylindrical moxa being removably inserted into said moxa holder from the rear end portion of the cylindrical body and forming a space between said cylindrical moxa and said cylindrical body in the front end portion of said cylindrical body;

a cap member having a rear end portion removably, rotatably and coaxially fitted to the front end portion of said cylindrical body to engage said cylindrical body, said cap member having a front wall for contact with affected body parts and an opening in said front wall communicating with said space formed between said cylindrical body and said cylindrical moxa for discharging combustion gas from firing said cylindrical moxa; and first air supply openings formed along the length of said cylindrical body between said rear end portion and said front end portion and second air supply openings formed along the length of and in said cap member where said cap member engages the front end portion of said cylindrical body, wherein said first and second air supply openings communicate with the space formed between said cylindrical moxa and said cylindrical body, the moxa holder of said cylindrical body comprises a metal and wherein said cylindrical body comprises an inside cylinder formed integrally around said moxa holder and a heat-insulator wound around said inside cylinder to a suitable thickness.

17. An acupressure-type moxibustion case according to claim 16, wherein the amount of air supplied to said space through said second air supply openings is varied from maximum to zero by rotating said cap member and said cylindrical body relative to each other.

18. An acupressure-type moxibustion case according to claim 16, wherein said moxa holder metal is aluminium and said heat insulator comprises asbestos cloth.

19. An acupressure-type moxibustion case according to claim 16, wherein said cylindrical body comprises two sections detachably connected to each other.

20. An acupressure-type moxibustion case according to claim 16, wherein said cylindrical moxa is wrapped in a strong thin paper and includes a longitudinal central through-hole therein.

* * * * *